United States Patent
Williams et al.

(10) Patent No.: US 6,624,422 B2
(45) Date of Patent: Sep. 23, 2003

(54) METHOD FOR DYNAMIC STABILIZATION OF PET DETECTOR GAINS

(75) Inventors: John Jay Williams, Hartland, WI (US); Kelly Alan Stonger, Waukesha, WI (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 214 days.

(21) Appl. No.: 09/963,148

(22) Filed: Sep. 25, 2001

(65) Prior Publication Data
US 2003/0057375 A1 Mar. 27, 2003

(51) Int. Cl.[7] .......................... G01T 1/164; G01T 1/208
(52) U.S. Cl. .................................. 250/363.09
(58) Field of Search ..................... 250/363.09

(56) References Cited

U.S. PATENT DOCUMENTS 5,677,536 A * 10/1997 Vickers ................. 250/363.09
5,986,266 A * 11/1999 Andreaco et al. ...... 250/363.09
6,232,604 B1 * 5/2001 McDaniel et al. ..... 250/363.03

* cited by examiner

Primary Examiner—Constantine Hannaher
(74) Attorney, Agent, or Firm—Quarles & Brady, LLP; Carl Horton (57) ABSTRACT

A method and apparatus for calibrating PET PMTs, the method including, during a commissioning process, determining gain factors for each crystal in a detector unit that cause the peak energy level in a crystal energy spectrum to be equal to a target value and, during a calibration process, generating energy spectrums for each crystal in the unit, combining the gain factors and crystal spectrums to generate shifted crystal spectrums, combining the shifted spectrums to generate a unit spectrum, identifying the peak unit spectrum energy level and comparing the peak unit level to the target value to generate PMT adjustment levels.

20 Claims, 6 Drawing Sheets

METHOD FOR DYNAMIC STABILIZATION OF PET DETECTOR GAINS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The present invention relates to PET scanners generally and specifically to a method and apparatus for adjusting PMT gains to compensate for drift due to various operating phenomenon.

Positrons are positively charged electrons which are emitted by radionuclides which have been prepared using a cyclotron or other device. The radionuclides most often employed in diagnostic imaging are fluorine-18, carbon-11, nitrogen-13 and oxygen-15. Radionuclides are employed as radioactive tracers called "radiopharmaceuticals" by incorporating them into substances such as glucose or carbon dioxide. One common use for radiopharmaceuticals is in the medical imaging field.

To use a radiopharmaceutical in imaging, the radiopharmaceutical is injected into a patient and accumulates in an organ, vessel or the like, which is to be imaged. It is known that specific radiopharmaceuticals become concentrated within certain organs or, in the case of a vessel, that specific radiopharmeceuticals will not be absorbed by a vessel wall. The process of concentrating often involves processes such as glucose metabolism, fatty acid metabolism and protein synthesis. Hereinafter, in the interest of simplifying this explanation, an organ to be imaged will be referred to generally as an "organ of interest" and prior art and the invention will be described with respect to a hypothetical organ of interest.

After a radiopharmaceutical becomes concentrated within an organ of interest and while the radionuclides decay, the radionuclides emit positrons. Each positron travels a very short distance before it encounters an electron and, when the positron encounters an electron, the positron is annihilated and converted into two photons, or gamma rays. This annihilation event is characterized by two features which are pertinent to medical imaging and particularly to medical imaging using photon emission tomography (PET). First, each gamma ray has an energy of essentially 511 keV upon annihilation. Second, the two gamma rays are directed in substantially opposite directions.

In PET imaging, if the general locations of annihilations can be identified in three dimensions, the shape of an organ of interest can be reconstructed for observation. To detect annihilation locations, a PET scanner is employed. An exemplary PET scanner includes one or more rings of detector modules and a processor which, among other things, includes coincidence detection circuitry. The detector modules are arranged about an imaging area. An exemplary detector module includes six adjacent detector blocks. An exemplary detector block includes an array of 36 bismuth germinate (BGO) scintillation crystals arranged in a 6×6 matrix and four photo-multiplier tubes (PMTs) arranged in a 2×2 matrix to the side of the crystal matrix opposite an imaging area.

When a photon impacts a crystal, the crystal generates light which is detected by the PMTs. The PMT signal intensities are combined to generate a combined analog signal which is converted into a digital signal. For the purposes of this explanation, it will be assumed that the digital value, also referred to as a target value, corresponding to 511 keV is 180. The combined digital signal is compared to a range of values about 511 keV. When the combined signal is within the range, an event detection pulse (EDP) is generated which is provided to the processor coincidence circuitry. In addition, acquisition circuits determine which crystal within a block absorbed the photon by comparing the relative strengths of the PMT signals.

The coincidence circuitry identifies essentially simultaneous EDP pairs which correspond to crystals which are generally on opposite sides of the imaging area. Thus, a simultaneous pulse pair indicates that an annihilation has occurred somewhere on a straight line between an associated pair of crystals. Over an acquisition period of a few minutes, millions of annihilations are recorded, each annihilation associated with a unique crystal pair. After an acquisition period, recorded annihilation data is used via any of several different well known procedures to construct a three dimensional image of the organ of interest.

While operation of a PET detector is relatively simple in theory, unfortunately, despite efforts to manufacture components that operate in an ideal fashion, there is an appreciable variation in how similar detector components respond to identical stimuli. For example, given a detector block including 36 crystals and four PMTs and given the same stimuli, crystals that are positioned proximate the center of the PMT array will typically generate a higher energy value than edge or corner crystals (i.e., crystals that are positioned along the edge of the array or at the corner of the array). This disparate and position dependent energy spectrum occurs because, typically, some of the light generated by an edge or corner crystal is not detected by the PMTs in a single block.

As one other example, even within a single crystal, impacting photons may not generate the same PMT output for various reasons. For instance, some photons are completely absorbed by a crystal while others are not. Completely absorbed photons generate light corresponding to 511 keV while partially absorbed photons generate less than the 511 keV. As another instance, first and second photons may be partially absorbed essentially simultaneously by first and second crystals in the same block. While each photon would be identified if they had been absorbed consecutively, upon simultaneous absorption, the combined energy may erroneously be attributed to a single absorbed photon. In this case detection circuitry may erroneously identify a third crystal between the first and second crystals as the detecting or absorbing crystal.

Thus, while each detected photon should ideally generate a signal having an energy level of 511 keV, in many cases detected photons generate much less energy. For this reason, the energy range used to determine if a combined digital PMT signal corresponds to a detected photon typically is assigned a relatively low threshold value. For instance, in an exemplary PET system the low end of the energy range may be a digital value of 35 corresponding to approximately 100 keV (i.e., any absorption even having an energy greater than 100 keV is assumed to correspond to a photon).

In addition to the potential errors described above, other sources of system error also occur. For instance, given two PMTs and identical stimuli (i.e., input light), a first PMT will typically generate a slightly different output signal than the second PMT. Exacerbating matters, over time PMT performance has been known to degrade due to aging related changes in structure. Further exacerbating matters, PMTs often operate differently when exposed to different operating parameters. For instance, PMT output signals have been known to vary as a function of temperature, ambient magnetic fields and other parameters that are relatively difficult or expensive to control.

To compensate for PMT construction and operating variances, the PET industry has developed various commissioning/calibration procedures and associated hardware and software. Generally, during a calibration procedure, a PET source having a known intensity is provided inside the PET imaging area and PMT signals generated thereby are collected. The collected PMT signals are compared to expected PMT signals and, where there is a difference between the collected and known signals, PMT gains are adjusted to compensate for the differences.

While calibration techniques like the one described above are useful, unfortunately, most calibration techniques require acquisition of massive amounts of data and hence an appreciable amount of time to complete. In addition, many calibration techniques include at least some manual steps that have to be performed by skilled technicians.

Because of the time and skills required to calibrate a PET system, in many cases, calibration will only be performed when absolutely necessary such as after image artifacts begin to appear in generated images. In other cases calibration is performed routinely whether or not the calibration is necessary. For instance, in some cases calibration is performed on a weekly basis. In the case of mobile PET systems (i.e., truck based systems), the system environment and, in particular, ambient magnetic fields, may change on a daily basis. In these cases calibration will typically be performed on a daily basis.

Thus, in some cases where calibration should be performed, calibration may be foregone until a later time while in other cases, where calibration is not necessary, a routine calibration procedure may be performed. In addition, in cases where calibration is only performed when a radiologist begins to recognize artifacts, the radiologist is routinely faced with the question of whether or not to recalibrate.

BRIEF SUMMARY OF THE INVENTION

An exemplary embodiment of the invention includes a method for calibrating PET detector PMT gains in a detector unit including at least one detector block, where a block includes a two dimensional crystal array including crystals arranged adjacent an imaging area and a PMT array including a two dimensional array of PMTs arranged adjacent the crystal array opposite the imaging area, a target energy level being associated with the known average energy of a photon, the method comprising the steps of providing a calibration photon source adjacent the at least one block during a calibration period. For each unit crystal the method further includes obtaining a calibration energy spectrum where the calibration spectrum indicates the number of detected photons at each of several possible energy levels and mathematically combining the calibration spectrum and a crystal specific gain factor to generate a shifted spectrum for the crystal. Thereafter, the method includes combining the shifted spectrums for all unit crystals to generate a unit spectrum, identifying a peak unit energy level for the unit spectrum where the peak unit energy level is the energy level at which the greatest number of photons was detected, comparing the peak unit energy level and the target energy level, based on the difference between the peak unit energy level and the target energy level, adjusting the PMT gains for the unit PMTs.

In at least one embodiment the method further includes the steps of, prior to the step of providing and during a commissioning procedure, providing a commissioning photon source adjacent the at least one block and during a commissioning period, for each unit crystal, obtaining a commissioning energy spectrum where the commissioning spectrum indicates the number of detected photons at each of several possible energy levels, identifying a peak energy level for the commissioning spectrum and mathematically combining the target energy level and the peak energy level to generate the crystal specific gain factor.

The step of mathematically combining to generate the gain factor may includes the step of dividing the target energy level by the peak energy level. Similarly, the step of mathematically combining to generate the shifted energy spectrum may include the step of multiplying each energy level within the spectrum by the crystal gain factor thereby shifting each of the energy level counts.

In addition to the method, the invention includes other similar methods and also contemplates an apparatus that includes either dedicated hardware or that may be implemented in software as computer programs that represent algorithms for execution by a conventional-type digital processor adapted for imaging applications.

These and other aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefore, to the claims herein for interpreting the scope of the invention.

DETAILED DESCRIPTION OF THE INVENTION

While various components are described below for carrying out several inventive methods, it should be appreciated that all of the methods herein may be performed by any of several different commercially available and programmable processors.

Referring now to the drawings, wherein like reference characters and symbols represent corresponding elements and signals throughout the several views, and more specifically referring to FIG. 1, the present invention will be described in the context of an exemplary PET scanner system 8. System 8 includes an acquisition system 10, an operator work station 15, acquisition, locator and coincidence (ALC) circuitry 30 and an image reconstruction processor 40.

System 10 includes a gantry 9 which supports a detector ring assembly 11 about a central bore which defines an imaging area 12. A patient table (not illustrated) is positioned in front of gantry 9 and is aligned with imaging area 12. A patient table controller (not shown) moves a table bed (not shown) into imaging area 12 in response to commands received from work station 15 through a serial communications link 18.

A gantry controller 17 is mounted within gantry 9 and is responsive to commands received from operator work station 15 through link 18 to operate gantry 9. For example, gantry 9 can be tilted away from vertical on command from an operator, can perform a "transmission scan" with a calibrated radio nuclide source to acquire attenuation measurements, can perform a "coincidence timing calibration scan" to acquire corrective data, or can perform a normal "emission scan" in which positron annihilation events are counted.

Figure 2:
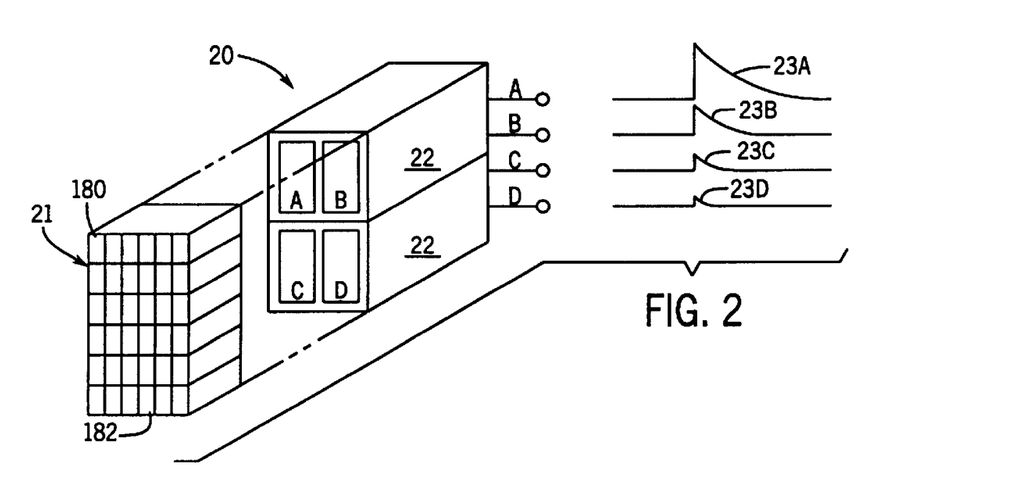
FIG. 2 is a perspective view of a detector unit and associated PMTs.

As shown best in FIG. 2, assembly 11 is comprised of a large number of detector blocks 20. Although not illustrated, detector blocks 20 are arranged in modules, each module including six separate and adjacent detector blocks 20. A typical assembly 11 includes 56 separate modules such that each assembly 11 includes 336 separate detector blocks 20. Each block 20 includes a set of bismuth germinate (BGO) scintillator crystals 21 (two separate crystals identified by numerals 180 and 182) arranged in a 6×6 matrix and disposed in front of four photo multiplier tubes (PMTs) A, B, C and D which are collectively referred to by numeral 22. When a photon impacts a crystal 21, a scintillation event occurs and the crystal generates light which is directed at PMTs 22. Each PMT 22 receives at least some light generated by the scintillation event and produces an analog signal 23A–23D which arises sharply when a scintillation event occurs and then tails off exponentially with a time constant of approximately 300 nanoseconds. The relative magnitudes of the analog signals 23A–23D are determined by the position in the 6×6 BGO matrix at which a scintillation event takes place, and the total magnitude of these signals is determined by the energy of an absorbed or partially absorbed photon which causes the event.

Figure 1:
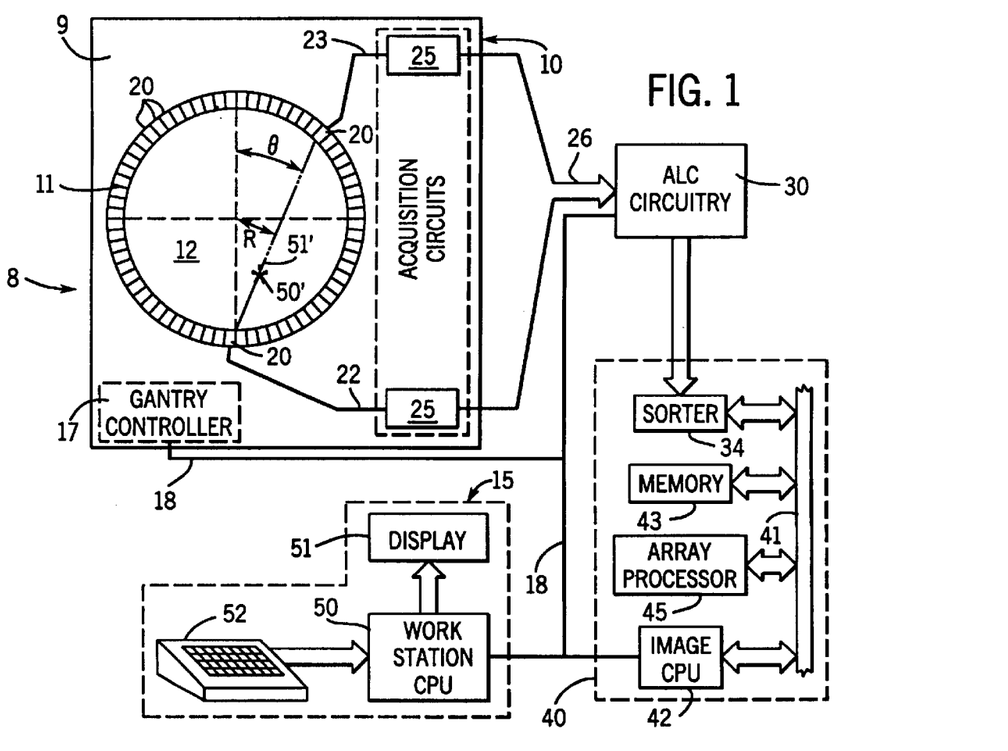
FIG. 1 is a schematic view of a PET system for implementing the present invention.

Referring still to FIGS. 1 and 2, a set of acquisition circuitry 25 is mounted within gantry 9 to receive the four signals 23A–23D from each detector block 20 in assembly 11. Circuitry 25 provides signals 23A–23D to ALC circuitry 30 via a data bus 26. Circuitry 30 uses the signals 23A–23D to determine the energy $E_i$ of a detected event, if the energy detected likely corresponds to a photon, the actual coordinates $C_i$ of a detected event within the block of BGO crystals 21, the time $T_i$ of the event (i.e. generates a time stamp) and compares event times to identify coincidence pairs of events that are stored as coincidence data packets. Each coincidence data packet includes a pair of digital numbers which precisely identify the addresses of the two BGO crystals 21 that detected an associated event. Operation of ALC circuitry 30 is explained more in detail below.

Referring again to FIG. 1, processor 40 includes a sorter 34, a memory module 43, an array processor 45, an image CPU 42 and a backplane bus 41 which conforms to the VME standards and links all other processor components together. The primary purpose of sorter 34 is to generate memory addresses for the coincidence data packets to efficiently store coincidence data. The set of all projection rays that point in the same direction and pass through the scanner's FOV is a complete projection, or "view". A distance R between a particular projection ray and a center of the FOV locates that projection ray within the FOV. As shown in FIG. 1, for example, a positron annihilation (hereinafter an "event") 50' occurs along a projection ray 51' which is located in a view at the projection angle θ and the distance R. Sorter 34 counts all of the events which occur on this projection ray (R, θ) during an acquisition period by sorting out the coincidence data packets that indicate an event at the two BGO detector crystals lying on ray 51'.

During data acquisition, the coincidence counts are organized in memory 43 as a set of two-dimensional arrays, one for each axial image, and each having as one of its dimensions the projection angle θ and the other dimension distance R. This θ by R histogram of detected events is called a sinogram. Coincidence events occur at random and sorter 34 quickly determines the θ and R values from the two crystal addresses in each coincidence data packet and increments the count of the corresponding sinogram array element. At the completion of an acquisition period, memory 43 stores the total number of annihilation events which occurred along each ray (R, θ) in the sinogram.

Image CPU 42 controls bus 41 and links processor 40 to local network 18. Array processor 45 also connects to the bus 41 and operates under the direction of image CPU 42 to facilitate image reconstruction using histogram data from memory module 43. The resulting image array is stored in memory module 43 and may be output by image CPU 42 to operator work station 15.

Station 15 includes a CPU 50, a CRT display 51 and a keyboard 52 or other similar input device (e.g., mouse, joystick, voice recognition module, etc.). CPU 50 connects to network 18 and scans key board 52 for input information. Through the keyboard 52 and associated control panel switches, an operator can control calibration of system 9, its configuration, and the positioning of a patient table during data acquisition.

Figure 3:
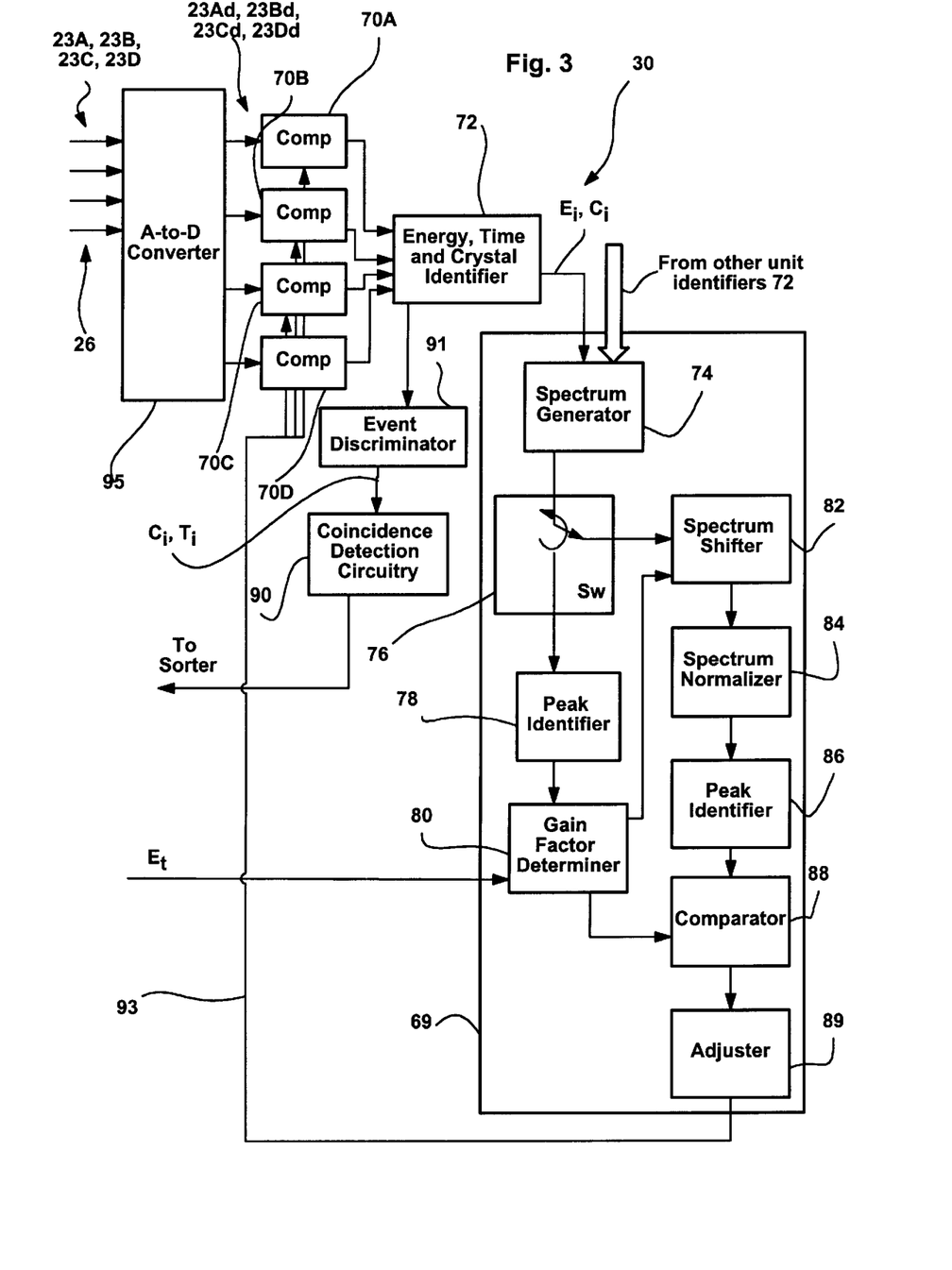
FIG. 3 is a schematic view of the ALC circuitry of FIG. 1.

Referring still to FIGS. 1 and 2 and also to FIG. 3, among other components for each block 20, exemplary and simplified ALC circuitry 30 includes an analog to digital (AD) converter 95, four compensators 70A, 70B, 70C and 70D, an energy, time and crystal identifier 72, coincidence detection circuitry 90 and event discriminator 91. A separate line (collectively identified by numeral 26) links each of PMTs 22 in a "unit" to the AD converter 95 which converts each of the analog signals 23A–23D to a digital signal 23Ad–23Dd. Consistent with the explanation and assumptions above, an analog signal corresponding to 511 keV is converted to a digital value 180, an analog signal corresponding to 100 keV is converted to a digital value 35, etc. Digital values 23Ad–23Dd are provided to compensators 70A–70D, respectively. Each compensator 70A–70D is separately adjustable so that the received digital signal (e.g., 23A) may be either increased or decreased to compensate for PMT degradation or varying operation due to ambient changes.

Compensator outputs are provided to identifier 72 which uses the received compensated PMT signals to identify event energy levels $E_i$, time $T_i$ at which each event occurs and which crystal $C_i$ absorbed the photon that caused the event. Methods and circuitry to perform each of these tasks are well known in the PET industry and therefore will not be explained here in detail. For a better understanding of how identifier 72 operates refer to U.S. Pat. No. 6,232,604 which is entitled Analog Time Adjustment for Coincidence Detection Electronics.

Referring still to FIGS. 1 through 3, the event times $T_i$, energies $E_i$ and crystal identifiers $C_i$ are provided to event discriminator 91 as distinct data packets. Discriminator 91 compares the event energies $E_i$ to a threshold energy level $E_{th}$ to identify data packets that likely correspond to valid absorbed photons. In the present example, it will be assumed that energy level $E_{th}$ is 100 keV corresponding to a digital value 35. Thus, discriminator identifies all packets having digital values between 35 (e.g., 100 keV) and 180 (e.g., 511 keV) and passes times $T_i$ and identifiers $C_i$ corresponding to those packets to coincidence detection circuitry 90.

Circuitry 90 compares the times $T_i$ in each packet to identify coincidence events. Where two even times $T_i$ are within a small period (i.e., within a "coincidence window") and if other criteria (e.g., corresponding crystals $C_i$ are separated by the system field of view (FOV)) are met, circuitry 90 identifies the packets as comprising to a "coincidence pair." Circuit 90 provides coincidence pairs to sorter 34 for further image processing as described above.

Hereinafter, in the interest of simplifying this explanation the term "unit" will be used to refer to 25 blocks 20. However, it should be appreciated that the invention contemplates other groupings of blocks. For instance, in some cases a unit may include two blocks 20, four blocks 20, all blocks 20 that reside in an upper half of detector 11, all blocks that reside in the lower half of detector 11, all blocks 20 within detector 11, etc. the smallest unit comprises a single block 20.

Referring to FIG. 3, ALC 30 also includes one or more calibrators 69. During each of a commissioning and a calibration process, calibrator 69 receives all energy $E_i$ and crystal identifier $C_i$ information from identifiers 73 (i.e., there is one identifier 72 for each block) corresponding to a single unit. Using the received information calibrator 69 calculates PMT signal adjustments used to adjust the output of compensators 70A–70D. Thus, in the present example, calibrator 69 receives signals from 25 separate blocks 20 (see also FIGS. 1 and 2).

Referring still to FIG. 3, calibrator 69 is used to perform two separate processes. A first process, referred to as a commissioning process, is to be performed once or perhaps very seldom (e.g., every month or quarter) to generate information that can be used subsequently during calibration processes. The second process, referred to as a calibration process, is meant to be performed routinely. For example, because the calibration process requires only minimal time to complete, it is contemplated that a PET system could perform the calibration process before every data acquisition procedure and in a manner that is imperceptible to both patient and operator. An exemplary commissioning procedure 92 is illustrated in FIG. 4 while an exemplary calibration procedure 114 is illustrated in FIG. 5

Referring still to FIG. 3, calibrator 69 includes a spectrum generator 74, a switch 76, a first peak identifier 78, a gain factor determiner 80, a spectrum shifter 82, a spectrum normalizer 84, a second peak identifier 86, a comparator 88 and an adjuster 89. While shown separately to simplify this explanation, identifiers 78 and 86 may comprise a single identifier. Generator 74 and switch 76 are used during both the commissioning and calibrating process, identifier 78 and determiner 80 are used during the commissioning process and shifter 82, normalizer 84, identifier 86, comparator 88 and adjuster 89 are used during the calibration process.

Figure 4:
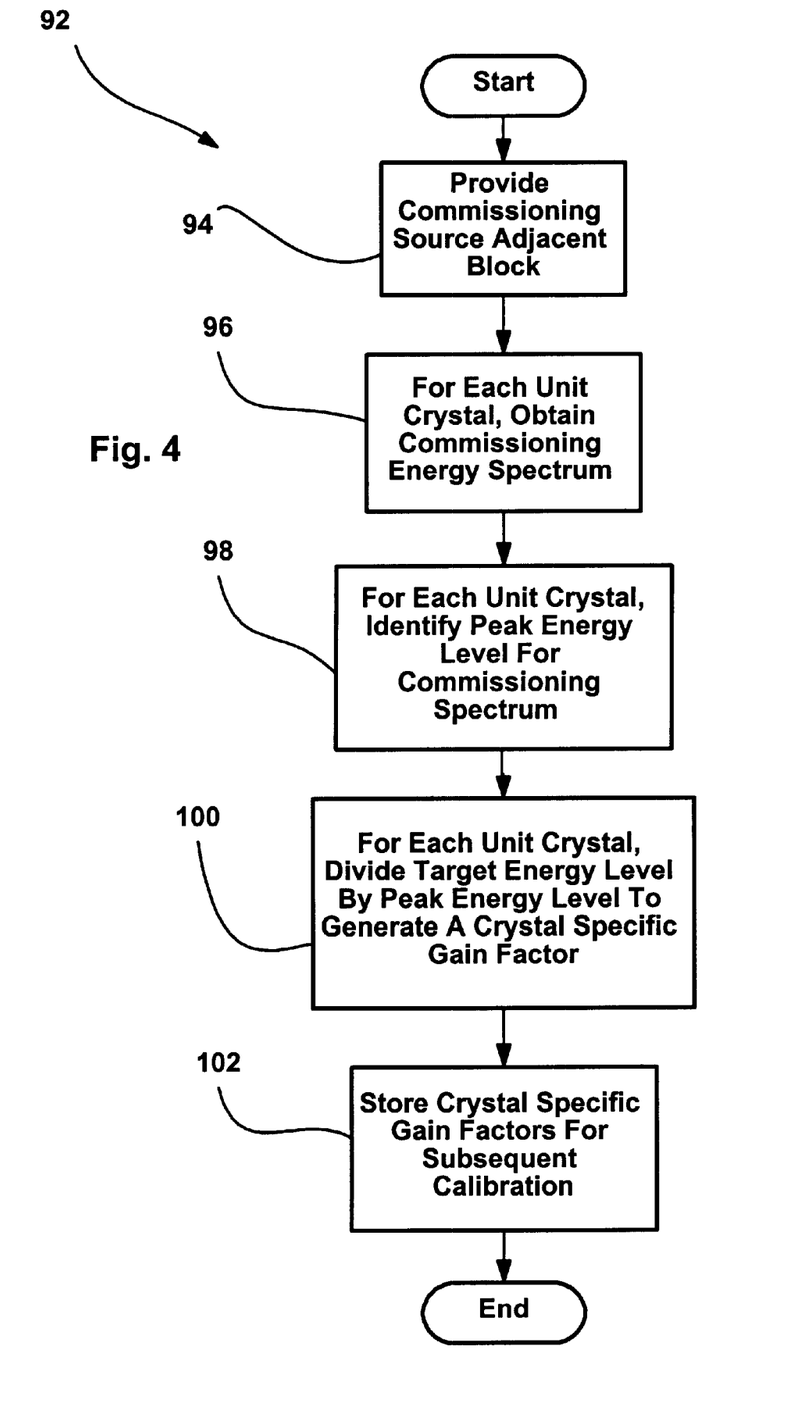
FIG. 4 is a flow chart illustrating a commissioning procedure.
Figure 5:
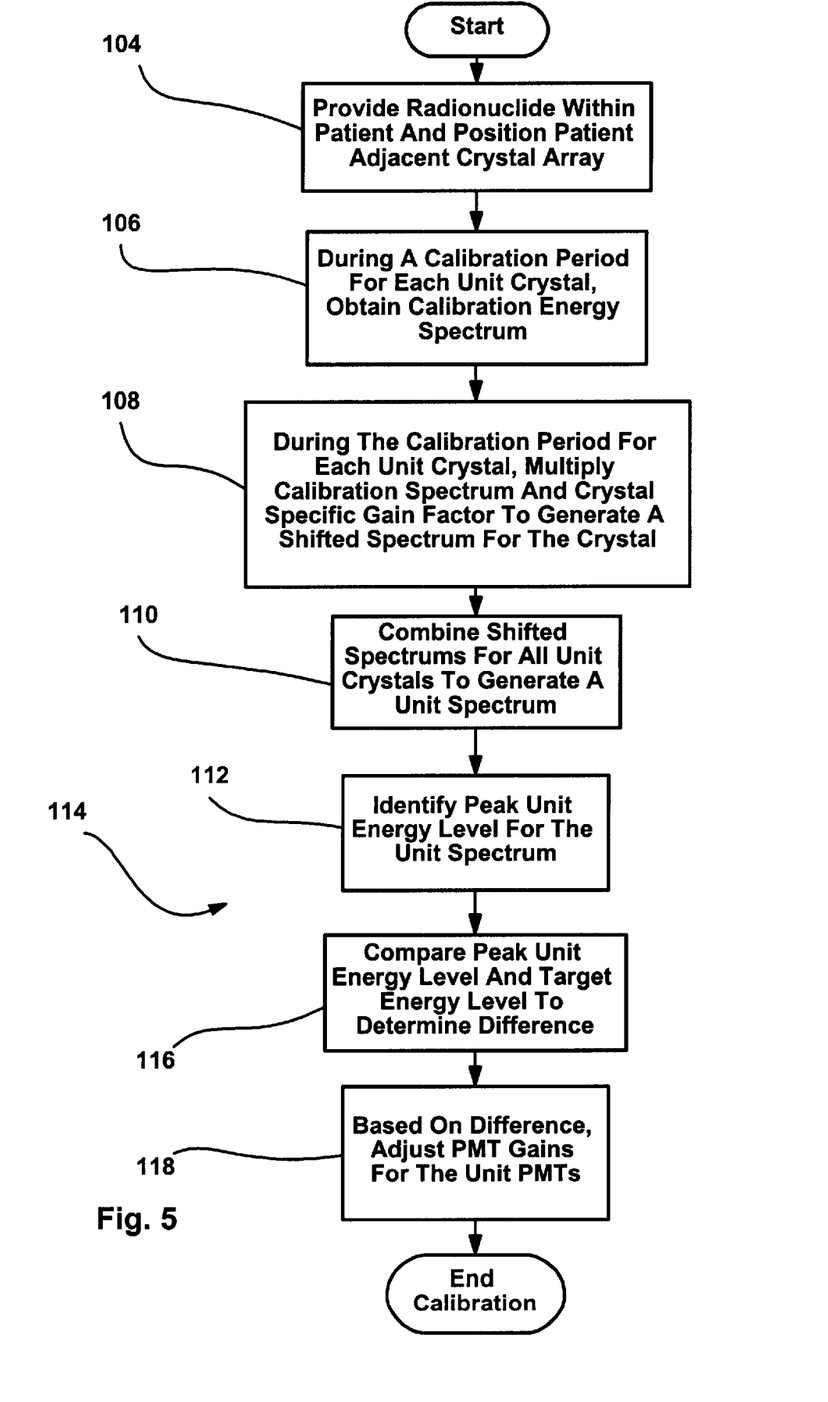
FIG. 5 is a flow chart illustrating a calibration procedure.

Referring to FIGS. 1, 3 and 4, at block 94 a commissioning photon source is provided within imaging area 12 adjacent detector blocks 20. The source (not illustrated) directs photons at blocks 20. For each absorbed photon, identifier 72 provides both the energy $E_i$ and the crystal identifier $C_i$ to spectrum generator 74. Throughout a commissioning period, generator 74 generates a separate commissioning energy spectrum for each crystal within the unit. Thus, for instance, referring again to FIG. 2, because a unit includes twenty-five blocks 20 in the present example and each block 20 includes 36 crystals (e.g., 180, 182, etc.), generator 74 generates 900 separate crystal spectrums for the exemplary unit.

Figure 6:
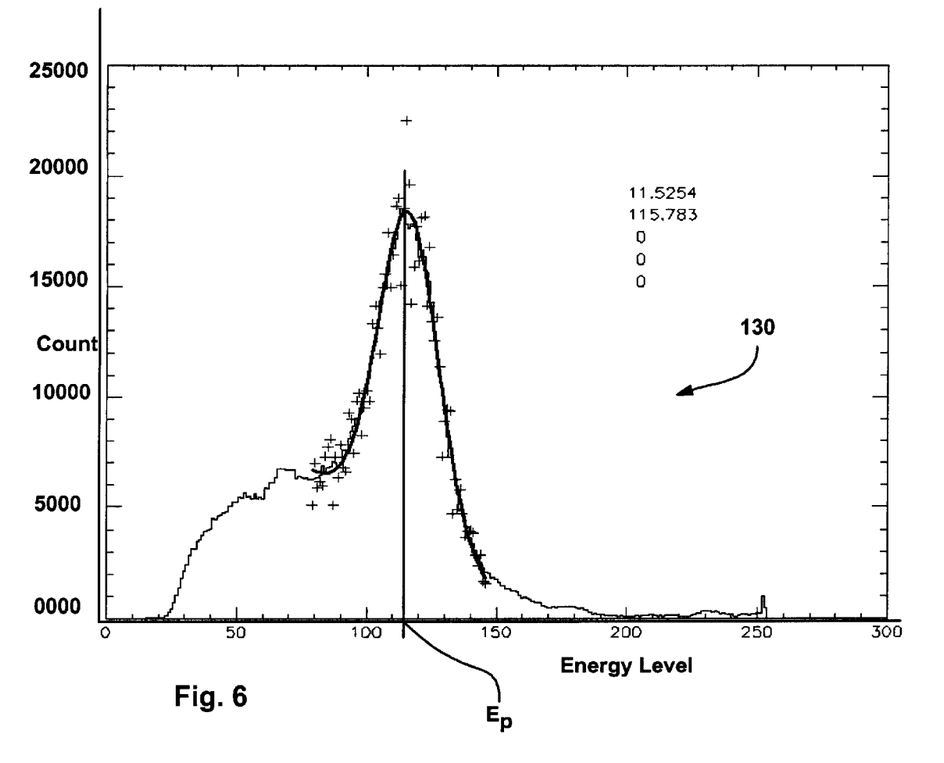
FIG. 6 is a graph illustrating a crystal spectrum generated during a commissioning procedure.

Referring now to FIG. 6, an exemplary commissioning spectrum 130 for a single crystal is illustrated. Referring also to FIG. 2, it will be assumed spectrum 130 corresponds to edge crystal 182. Each spectrum 130 plots the number of photons absorbed by a corresponding crystal at specific energy levels on a vertical axis against energy level (i.e., $E_i$) on a horizontal axis. For instance, in exemplary spectrum 130 in FIG. 6, approximately five thousand absorbed photons had energy levels corresponding to a digital count of 80, approximately twenty thousand absorbed photons had energy levels corresponding to a count of 120 and approximately two thousand photons had energy levels corresponding to a count of 148. to generate a spectrum 130 generator 74 simply maintains counters for each possible digital energy value for each crystal and increments the appropriate counter when a photon energy level $E_i$ matches the level associated with the counter.

Exemplary commissioning spectrum 130 clearly illustrates that the energies $E_i$ attributed to separate absorbed photons vary widely even within a given crystal due to phenomenon described above including partial absorption, dual absorption, partial light detection, etc. Clearly there is a peak energy level $E_p$ at which a curve through the count values is at a highest point. In spectrum 130 the peak energy level occurs at approximately 115.

As indicated above, the digital value attributable to a completely absorbed and detected photon is 180 (corresponding to 511 keV). Given this assumption, the peak energy level 115 seams to be relatively low as one would expect the peak level to have been approximately 180. As it turns, crystal 182 (see FIG. 2) to which exemplary spectrum 130 corresponds is an edge crystal (i.e., a crystal residing along an edge of a corresponding block 20) which means much of the light generated thereby is not detected by PMTs. A spectrum corresponding to a more centrally located crystal (i.e., a crystal near the center of array 21 in FIG. 2) would have a peak energy level almost exactly at 180.

Referring again to FIGS. 1, 3 and 4, during the commissioning procedure switch 76 is closed to identifier 78. At block 98, for each unit crystal, identifier 78 determines the peak energy level $E_p$ of the corresponding commissioning spectrum 130. Once again, for the spectrum 130 in FIG. 6, the peak level is approximately 115. The peak levels are provided to determiner 80.

Determiner 80 also receives an energy target input $E_t$ which indicates a target energy level for each crystal that corresponds to 511 keV. The target level in the present case is 180 which is provided by a system 8 user.

At step 100, determiner 80 combines the target energy level $E_t$ with each of the separate peak energy levels $E_p$ for each crystal thereby generating a separate gain factor $G_f$ for each unit crystal. This combining step includes dividing the target level $E_t$ by each of the peak levels $E_p$. For instance, in the case of the crystal corresponding to spectrum 130 in FIG. 6 with a peak level $E_p$ of 115, the gain factor $G_f$ would be 1.57 (i.e., 180 115=1.57). The gain factor $G_f$ is a factor by which the energies in the commissioning spectrum for the corresponding crystal have to be shifted in order for a shifted peak energy level $E_p$ to be equal to the target energy level $E_t$. Thus, in the present example, by multiplying each energy level in spectrum 130 by factor $G_f$=1.57, a compensated spectrum having a desired peak at 180 results.

The gain factors $G_f$ are stored for each separate crystal at step 102. During calibration, factors $G_f$ are provided to shifter 82.

Referring now to FIGS. 1, 3 and 5, after the commissioning procedure has been completed and gain factors $G_f$ for each crystal stored and prior to each data acquisition procedure, calibration process 114 is performed to adjust compensators 70A through 70D.

At block 104 a radionuclide is provided within a patient for imaging purposes and the patient is positioned within area 12 adjacent detector block 20 and, specifically, adjacent the 25 block unit in the present example so that photons are directed at unit crystals during the calibration process. It has been found that when a patient who has been injected with a radionuclide is near an imaging bore, even 0.1 millicurie of activity results in a block count rate of approximately 200 counts per second. It has also been found that approximately 5000 counts are needed in a spectrum to provide desired precision. In the present case, where the unit includes 25 blocks, for the entire unit, 5000 counts can be obtained in approximately one second. Thus, in the present case, the data acquisition portion of the calibration process would only require approximately one second.

Referring still to FIGS. 1, 3 and 5, at block 106, during a calibration period, generator 74 receives the energy $E_i$ and crystal identifier $C_i$ signals for every crystal within the unit and generates a separate calibration energy spectrum for each separate crystal. The calibration spectrums are similar to commissioning spectrum 130 in FIG. 6 plotting counts against energy values $E_i$ to form the spectrum. The primary difference between the calibration and commissioning spectrums generally is that the count values will be much greater for the commissioning spectrum than for the calibration spectrum because the commissioning period (e.g., several minutes) is much longer than the calibration period (e.g., 1 or 2 seconds). During calibration switch 76 is open to identifier 78 and closed to shifter 82.

At block 108, after the calibration spectrums have been generated and stored for each unit crystal, spectrum shifter 82 receives the spectrums and the crystal specific gain factors $G_f$ and multiplies the energy levels in the calibration spectrum by the gain factors $G_f$. For instance, assume that it has been some time since the commissioning procedure was performed to generate the gain factors $G_f$ and that crystal performance has degraded somewhat. In this case, a calibration spectrum for crystal 182 may have slid such that a peak energy level for the calibration spectrum is approximately 110 (i.e., the peak has slid 5 from the peak level of the commissioning spectrum). Here, the multiplying step 108 would multiply the calibration spectrum for crystal 182 by crystal specific gain factor 1.57 thereby shifting the entire calibration spectrum and generating a shifted spectrum for the crystal.

Thus, upon shifting, the peak energy level for the shifted spectrum will be similar to value 180. In the present case, the peak level for the shifted spectrum would have a value 172.7. Other spectrum energy levels are similarly shifted by factor 1.57.

It should be appreciated that, while crystal specific data collected during a short calibration acquisition is used to generate a crystal specific spectrum, because only a small amount of data (e.g., 2–3 hundred counts) for the crystal can be collected during the short calibration period, the crystal specific spectrum alone is not statistically very inaccurate.

Figure 7:
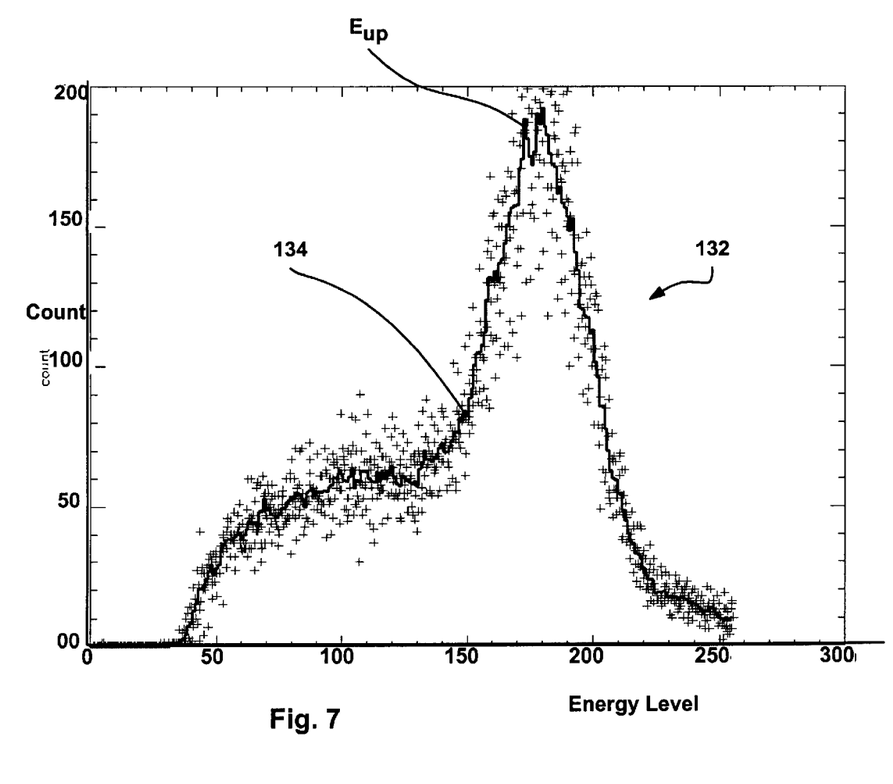
FIG. 7 is a graph illustrating a combined unit spectrum generated during a calibration procedure.

At block 110 normalizer 84 receives the shifted spectrums from each unit crystal and combines all of the data corresponding to the shifted spectrums into a single normalized unit spectrum. An exemplary unit spectrum 132 is illustrated in FIG. 7 where all of the data points from the separate crystal spectrum are overlaid onto a single graph and a curve 134 is formed therefrom. In FIG. 7 it can be seen that the peak energy level of the unit spectrum 132 is approximately 175.

Continuing, at block 112, identifier 86 determines the peak unit energy level $E_{up}$ for the unit spectrum.

At block 116, comparator 88 compares the peak unit energy value $E_{pu}$ (e.g., 175 in the present example) with the target energy value $E_t$ (e.g., 180) and determines the percent difference between the two values. For instance, in the present case, where the peak unit value $E_{pu}$ is 175 and the target value is 180, the difference is approximately 2.78%.

The difference value is provided to adjuster 89 which, at block 118, adjusts the PMT gains for all of the unit PMTs via compensators 70A–70D to increase the gains as a function of the difference value. In order to avoid oscillations, adjuster will typically be set to modify the PMT gains by a percentage of the difference value. For example, an exemplary percentage may be 75% so that, where the difference value is 2.78%, the adjustments would increase gains by 2.09%.

It should be appreciated that, while insufficient counts are collected on a crystal by crystal basis to provide statistical certainty required for spectral analysis, where counts from many crystals are combined, the number of counts is sufficient to facilitate acceptable accuracy despite a short (e.g., one second) calibration acquisition period. Thus, calibration can be performed quickly, relatively accurately and without operator interaction.

It should be understood that the methods and apparatuses described above are only exemplary and do not limit the scope of the invention, and that various modifications could be made by those skilled in the art that would fall under the scope of the invention.

To apprise the public of the scope of this invention, the following claims are made:

What is claimed is:

1. A method for calibrating PET detector PMT gains in a detector unit including at least one detector block, where a block includes a two dimensional crystal array including crystals arranged adjacent an imaging area and a PMT array including a two dimensional array of PMTs arranged adjacent the crystal array opposite the imaging area, a target energy level being associated with the known average energy of a photon, the method comprising the steps of:

providing a calibration photon source adjacent the at least one block during a calibration period and, for each unit crystal:
(i) obtaining a calibration energy spectrum where the calibration spectrum indicates the number of detected photons at each of several possible energy levels; and
(ii) mathematically combining the calibration spectrum and a crystal specific gain factor to generate a shifted spectrum for the crystal;

combining the shifted spectrums for all unit crystals to generate a unit spectrum;

identifying a peak unit energy level for the unit spectrum where the peak unit energy level is the energy level at which the greatest number of photons was detected;

comparing the peak unit energy level and the target energy level; and based on the difference between the peak unit energy level and the target energy level, adjusting the PMT gains for the unit PMTs.

2. The method of claim 1 further including the steps of, prior to the step of providing and during a commissioning procedure:

providing a commissioning photon source adjacent the at least one block and during a commissioning period, for each unit crystal:

(i) obtaining a commissioning energy spectrum where the commissioning spectrum indicates the number of detected photons at each of several possible energy levels;

(ii) identifying a peak energy level for the commissioning spectrum; and (iii) mathematically combining the target energy level and the peak energy level to generate the crystal specific gain factor.

3. The method of claim 2 wherein the step of providing the calibration source includes the steps of providing a radionuclide within a patient and positioning the patient adjacent the crystal array.

4. The method of claim 2 wherein the step of mathematically combining to generate the gain factor includes the step of dividing the target energy level by the peak energy level.

5. The method of claim 4 wherein the step of mathematically combining to generate the shifted energy spectrum includes the step of multiplying each energy level within the spectrum by the crystal gain factor thereby shifting each of the energy level counts.

6. The method of claim 5 wherein the step of comparing includes the step of determining the percentage difference between the peak unit energy level and the target energy level and wherein the step of adjusting includes the step of adjusting the gain of each of the PMTs in a manner calculated to modify the gains by the percentage difference.

7. The method of claim 1 wherein the unit is a first unit and the PET detector includes at least a second unit and wherein the process is performed simultaneously for each detector unit to adjust unit PMT gains.

8. The method of claim 7 wherein the first unit is positioned above the second unit in the detector.

9. The method of claim 1 wherein the calibration period is between one half second and ten seconds.

10. A method for calibrating PET detector PMT gains in a detector unit including at least one detector block, where a block includes a two dimensional crystal array including crystals arranged adjacent an imaging area and a PMT array including a two dimensional array of PMTs arranged adjacent the crystal array opposite the imaging area, a target energy level being associated with the known average energy of photon, the method comprising the steps of:

(A) providing a commissioning photon source adjacent the at least one lock and, during a commissioning period, for each unit crystal:

(i) obtaining a commissioning energy spectrum where the commissioning spectrum indicates the number of detected photons at each of several possible energy levels;

(ii) identifying a peak energy level for the commissioning spectrum at which the greatest number of photons was detected; and (iii) mathematically combining the target energy level and the peak energy level to generate a crystal specific gain factor;

(B) providing a radionuclide within a patient and positioning the patient adjacent the crystal array and, during a calibration period, for each unit crystal:

(i) obtaining a calibration energy spectrum where the calibration spectrum indicates the number of detected photons at each of several possible energy levels; and (ii) mathematically combining the calibration spectrum and the crystal specific gain factor to generate a shifted spectrum for the crystal;

combining the shifted spectrums for all unit crystals to generate a unit spectrum;

identifying a peak unit energy level for the unit spectrum;

comparing the peak unit energy level and the target energy level; and based on the difference between the peak unit energy level and the target energy level, adjusting the PMT gains for the unit PMTs.

11. The method of claim 10 wherein the step of mathematically combining to generate the gain factor includes the step of dividing the target energy level by the peak energy level.

12. The method of claim 11 wherein the step of mathematically combining to generate the shifted energy spectrum includes the step of multiplying each energy level within the spectrum by the crystal gain factor thereby shifting each of the energy level counts.

13. An apparatus for calibrating PET detector PMT gains in a detector unit including at least one detector block, where a block includes a two dimensional crystal array including crystals arranged adjacent an imaging area and a PMT array including a two dimensional array of PMTs arranged adjacent the crystal array opposite the imaging area, a target energy level being associated with the known average energy of a photon, the apparatus comprising:

means for providing a calibration photon source adjacent the at least one block during a calibration period and, for each unit crystal:

(i) means for obtaining a calibration energy spectrum where the calibration spectrum indicates the number of detected photons at each of several possible energy levels; and (ii) means for mathematically combining the calibration spectrum and a crystal specific gain factor to generate a shifted spectrum for the crystal;

means for combining the shifted spectrums for all unit crystals to generate a unit spectrum;

means for identifying a peak unit energy level for the unit spectrum where the peak unit energy level is the energy level at which the greatest number of photons was detected;

means for comparing the peak unit energy level and the target energy level; and means for, based on the difference between the peak unit energy level and the target energy level, adjusting the PMT gains for the unit PMTs.

14. The apparatus of claim 13 further including the steps of, prior to the step of providing and during a commissioning procedure:

providing a commissioning photon source adjacent the at least one block and during a commissioning period, for each unit crystal:
  (i) obtaining a commissioning energy spectrum where the commissioning spectrum indicates the number of detected photons at each of several possible energy levels;
  (ii) identifying a peak energy level for the commissioning spectrum; and
  (iii) mathematically combining the target energy level and the peak energy level to generate the crystal specific gain factor.

15. The apparatus of claim 14 wherein the means for mathematically combining to generate the gain factor includes means for dividing the target energy level by the peak energy level.

16. The apparatus of claim 15 wherein the means for mathematically combining to generate the shifted energy spectrum includes means for multiplying each energy level within the spectrum by the crystal gain factor thereby shifting each of the energy level counts.

17. An apparatus for calibrating PET detector PMT gains in a detector unit including at least one detector block, where a block includes a two dimensional crystal array including crystals arranged adjacent an imaging area and a PMT array including a two dimensional array of PMTs arranged adjacent the crystal array opposite the imaging area, a target energy level being associated with the known average energy of a photon, the apparatus comprising:

a processor for performing a pulse sequencing program to perform the steps of:
  providing a calibration photon source adjacent the at least one block during a calibration period and, for each unit crystal:
    (i) obtaining a calibration energy spectrum where the calibration spectrum indicates the number of detected photons at each of several possible energy levels; and
    (ii) mathematically combining the calibration spectrum and a crystal specific gain factor to generate a shifted spectrum for the crystal;
  combining the shifted spectrums for all unit crystals to generate a unit spectrum;
  identifying a peak unit energy level for the unit spectrum where the peak unit energy level is the energy level at which the greatest number of photons was detected;
  comparing the peak unit energy level and the target energy level; and
  based on the difference between the peak unit energy level and the target energy level, adjusting the PMT gains for the unit PMTs.

18. The apparatus of claim 17 wherein the pulse sequencing program further causes the processor to perform the steps of, prior to the step of providing and during a commissioning procedure:

providing a commissioning photon source adjacent the at least one block and during a commissioning period, for each unit crystal:
  (i) obtaining a commissioning energy spectrum where the commissioning spectrum indicates the number of detected photons at each of several possible energy levels;
  (ii) identifying a peak energy level for the commissioning spectrum; and
  (iii) mathematically combining the target energy level and the peak energy level to generate the crystal specific gain factor.

19. The apparatus of claim 18 wherein, to perform the step of mathematically combining to generate the gain factor the program causes the processor to perform the step of dividing the target energy level by the peak energy level.

20. The apparatus of claim 19 wherein, to perform the step of mathematically combining to generate the shifted energy spectrum the program causes the processor to perform the step of multiplying each energy level within the spectrum by the crystal gain factor thereby shifting each of the energy level counts.

* * * * *

UNITED STATES PATENT AND TRADEMARK OFFICE
CERTIFICATE OF CORRECTION

PATENT NO. : 6,624,422 B2
DATED : September 23, 2003
INVENTOR(S) : Williams et al.

It is certified that error appears in the above-identified patent and that said Letters Patent is hereby corrected as shown below:

Column 11,
Line 60, "of photon" should be -- of a photon --.
Line 62, "lock" should be -- block --.

Signed and Sealed this

Fifteenth Day of June, 2004

JON W. DUDAS
*Acting Director of the United States Patent and Trademark Office*